United States Patent
Hackl

(10) Patent No.: US 10,598,716 B2
(45) Date of Patent: Mar. 24, 2020

(54) METHODS AND LOCATING SYSTEMS FOR DETERMINING AN INSULATION FAULT LOCATION ON AN ELECTRIC CONDUCTOR OF A SUBSEA SUPPLY LINE

(71) Applicant: Bender GmbH & Co. KG, Gruenberg (DE)

(72) Inventor: Dieter Hackl, Fernwald (DE)

(73) Assignee: BENDER GMBH & CO. KG, Gruenberg (DE)

( * ) Notice: Subject to any disclaimer, the term of this patent is extended or adjusted under 35 U.S.C. 154(b) by 347 days.

(21) Appl. No.: 15/620,999

(22) Filed: Jun. 13, 2017

(65) Prior Publication Data
US 2017/0370981 A1 Dec. 28, 2017

(30) Foreign Application Priority Data
Jun. 28, 2016 (DE) .................. 10 2016 211 651

(51) Int. Cl.
*G01R 31/08* (2020.01)
*H02G 1/10* (2006.01)
(Continued)

(52) U.S. Cl.
CPC ............ *G01R 31/083* (2013.01); *G01H 3/06* (2013.01); *G01N 29/42* (2013.01); *H02G 1/10* (2013.01);
(Continued)

(58) Field of Classification Search
CPC .............. G01R 31/083; G01R 31/1209; G01R 31/1218; G01R 31/086; G01R 31/11; G01H 3/06; G01N 29/42
See application file for complete search history.

(56) References Cited

U.S. PATENT DOCUMENTS 5,256,976 A * 10/1993 Ishikawa ............ G01R 31/1254
174/11 R
2010/0280773 A1 11/2010 Saether
(Continued)

FOREIGN PATENT DOCUMENTS

AU 000006291273 11/1973
CN 101694183 A 4/2010
(Continued)

OTHER PUBLICATIONS

English machine translation of CN101694183A.
(Continued)

*Primary Examiner* — Elias Desta
(74) *Attorney, Agent, or Firm* — King & Schickli, PLLC

(57) ABSTRACT

Methods and locating systems are for determining an insulation fault location on an electric conductor of a subsea supply line. By applying electric voltage on the electric conductor, an electrochemical reaction takes place at an insulation fault location between the metallic conductor material and the seawater, the electrochemical reaction forming gas, which in turn is connected to developing noise. Sonic sensors capture the sonic waves produced inside and outside the subsea supply line and evaluate the measuring signals in order to determine the insulation fault location. Alternatively or additionally to capturing noise, the gas-bubble image patterns occurring at the insulation fault location are optically captured and consulted in order to determine the insulation fault location.

10 Claims, 4 Drawing Sheets

Figure 1:
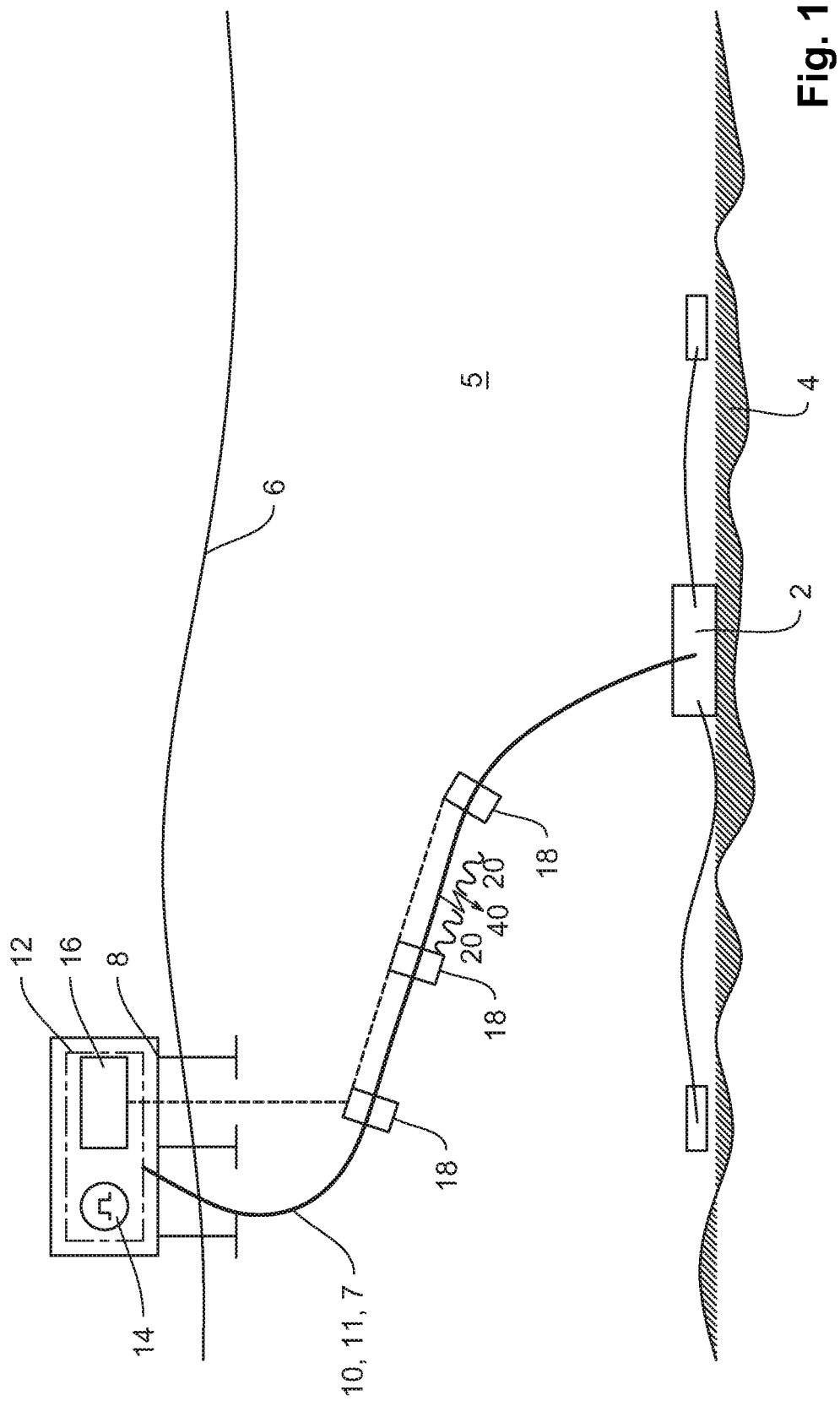

(51) Int. Cl.
*G01H 3/06* (2006.01)
*G01N 29/42* (2006.01)
*G01R 31/12* (2020.01)

(52) U.S. Cl.
CPC ...... *G01R 31/1209* (2013.01); *G01R 31/1218* (2013.01)

(56) References Cited

U.S. PATENT DOCUMENTS

| | | | |
|---|---|---|---|
| 2011/0114412 | A1 | 5/2011 | De Lorenzo et al. |
| 2014/0283585 | A1 | 9/2014 | Sæther |
| 2018/0045768 | A1* | 2/2018 | Godfrey ............... G01R 31/083 |

FOREIGN PATENT DOCUMENTS

| | | |
|---|---|---|
| CN | 101724439 A | 6/2010 |
| CN | 102053145 A | 5/2011 |
| CN | 102393245 A | 3/2012 |
| CN | 102964668 A | 3/2013 |
| CN | 103782147 A | 5/2014 |
| CN | 105277853 A | 1/2016 |
| DE | 19716963 | 10/1998 |
| DE | 112012003206 | 7/2014 |
| EP | 1320737 B1 | 7/2004 |
| JP | S5842979 Y2 | 3/1983 |
| JP | S5842980 A | 3/1983 |
| JP | S5842980 Y2 | 3/1983 |
| JP | 2008233600 A | 10/2008 |
| WO | WO8707949 | 12/1987 |
| WO | 2011052890 A2 | 5/2011 |
| WO | WO2011052890 A2 | 5/2011 |
| WO | WO2014128439 A1 | 8/2014 |

OTHER PUBLICATIONS

English machine translation of CN101724439A.
English machine translation of CN102053145A.
English machine translation of CN102393245A.
English machine translation of CN102964668A.
English machine translation of CN103782147A.
English machine translation of CN105277853.
English machine translation of CN105277853A.
English machine translation of JP2008233600A.
English machine translation of JPS5842980A.
English machine translation of WO2011/052890.

* cited by examiner

METHODS AND LOCATING SYSTEMS FOR DETERMINING AN INSULATION FAULT LOCATION ON AN ELECTRIC CONDUCTOR OF A SUBSEA SUPPLY LINE

This application claims the benefit of German Patent Application no. 10 2016 211 651.7 filed Jun. 28, 2016, the disclosure of which is incorporated herein by reference.

TECHNICAL FIELD

The invention relates to methods and locating systems for determining an insulation fault location on an electric conductor of a subsea supply line.

BACKGROUND

In the deep-sea oil and gas production, the oil and gas fields on the bottom of the sea are supplied with electric energy, pressure pipelines and command information via branched subsea supply lines, so-called umbilicals, originating from a central production platform. The expansion of oil and gas fields is so large that individual subsea supply lines can reach lengths of up to 150 km.

A subsea supply line failing can lead not only to significant economical shortages caused by production downtime but also to great risks to the environment, the production plant and the personnel on the plant caused by production installations which have become uncontrollable.

Identifying and quickly localizing damage to the subsea supply line, in particular insulation faults on an electric conductor run in the subsea supply line, are therefore a very high priority especially in the scope of supply lines.

The technology available for solving these safety related tasks, however, is limited by the specific requirements posed by the deep sea surroundings. This explains why insulation faults on electric conductors run in the subsea supply line are mostly localized manually by sending out divers, small submarines and ships. The expenditure and thus the costs of locating faults are accordingly high.

Methods of time domain reflectometry (TDR) for localizing faults on an electric conductor by means of reflected measuring signals are known from the state of the art. Using TDR technology, however, seems to be limited to pipe sections having a maximum length of 50 km with currently available technology.

Building upon the realization that electrolytic processes take place at a faulty insulation point between the exposed metallic conductor material, such as copper, and the saline seawater under the influence of an applied DC voltage when an electric line is run in the seawater, a regeneration method was proposed in the patent disclosure WO 2014/128439 A1, which uses the electrochemical reaction for repairing insulation fault locations. By periodically varying the amplitude of the DC voltage and by optionally changing the polarity, the process of forming gas at the faulty location during electrolysis can be influenced such that the insulation properties can be repaired. A targeted tracking of the insulation fault location was not disclosed.

SUMMARY

The object of the invention at hand is therefore to propose a method and a locating system, by means of which an insulation fault location can be determined on an electric conductor of a subsea supply line in a reliable and economically feasible manner.

For a subsea supply line, which can be filled with water, the object is attained by a first method, which comprises the following method steps: applying electric voltage to ground at the electric conductor, an electrochemical reaction taking place at the insulation fault location between a metallic conductor material of the electric conductor and the seawater, said electrochemical reaction forming gas, and the electric voltage being formed by a modulated voltage impulse sequence; capturing sonic waves of a noise made by formed gas bubbles, sonic waves of the noise propagating within the subsea supply line in the seawater filling being captured using sonic sensors, which are installed at predetermined locations along the subsea supply line; and evaluating measuring-signal impulse sequences supplied by the sonic sensors in order to determine the insulation fault location.

Effects, which so far remain unused in the state of the art, in the electrochemical reaction between the metallic conductor material and the saline seawater are those effects which form gas bubbles, which result from gas formation, in the seawater surrounding the insulation fault location and which observe the noise development connected to the gas bubble formation.

The basic concept of the first method according to the invention therefore rests upon the notion that the gas bubble formation is connected to noise and that the sonic waves resulting therefrom can be captured in a subsea supply line filled with seawater using sonic sensors. This first solution presumes that the subsea supply line is filled seawater in order to reduce buoyancy and to make installation easier. In consequence of the electrochemical reaction with the gas formation, the resulting gas bubble formation at the insulation fault location functions as a sonic source whose emitted sonic waves expand directed in the seawater filling and can be captured using sonic sensors.

Due to the electric voltage being formed by a modulated voltage impulse sequence, a temporal change in the applied voltage takes place, said temporal change being displayed in the captured sonic waves (and in the captured gas bubble patterns, cf. third method). By changing a modulation parameter, such as amplitude, frequency or phase, or due to differing modulation methods, respectively, the electrolytic process and thus the gas bubble formation are influenced in such a manner that the resulting noise and gas bubble patterns significantly differ to other possible noises and gas bubble formations.

Sonic sensors are installed at known and predetermined locations along the subsea supply line, said sonic sensors recording the sonic waves and converting these into measuring-signal impulse sequences. These measuring-signal impulse sequences are mathematically evaluated in order to determine the insulation fault location via a running-time measurement between noise development (presumed here as being simultaneous to the application of electric voltage) and noise capture in full awareness of the sensor locations and taking into account the speed of sonic propagation.

In an advantageous embodiment, the measuring-signal impulse sequences are evaluated by calculating a correlation of the applied voltage impulse sequence with the measured measuring-signal impulse sequences.

The electric voltage generated as a modulated voltage impulse sequence comprises a characteristic temporal progression, which is reflected in the temporal and spatial progression of the sonic waves. The measuring-signal impulse sequences generated by the sonic sensors therefore also show a characteristic temporal progression so that the received sonic signals can be identified by calculating the correlation of the applied voltage impulse sequence with the measured measuring-signal impulse sequences.

For a subsea supply line, which can be filled with seawater, the object is attained by a second method, which comprises the following method steps: applying electric voltage to ground at the electric conductor, an electrochemical reaction taking place at the insulation fault location between a metallic conductor material of the electric conductor and the seawater, said electrochemical reaction forming gas, and said electric voltage being formed by a modulated voltage impulse sequence; capturing sonic waves of a noise made by formed gas bubbles, sonic waves of the noise being captured outside of the subsea supply line using sonic sensors, which are installed at predetermined locations in the seawater; and evaluating measuring-signal impulse sequences supplied by the sonic sensors in order to determine the insulation fault location.

This second solution also rests upon the notion of the effect causing noise propagation, namely the effect of the electrochemical reaction, which is caused by a modulated electric voltage, between the metallic conductor material and the saline seawater, which immediately surrounds the electric conductor in the subsea supply line filled with seawater. The gas bubble formation resulting therefrom in turn is the cause for the sonic wave generation in the seawater surrounding the electric conductor.

However, it is not the directed sonic wave propagation within the seawater filling of the subsea supply line which is observed in this second method but rather it is presumed that the sonic waves also propagate mostly undirected in the seawater outside of the subsea supply line. There, they are captured using sonic sensors, which are installed at known and predetermined locations. In particular in subsea supply lines, which are provided with through bores (perforations used for flooding with seawater), the sonic waves not only propagate indirectly via oscillations of the outer casing of the subsea supply line but also exit directly from the perforations of the outer casing.

The measuring-signal impulse sequences generated by the sonic sensors are mathematically evaluated analogously to the first method via a running-time measurement between noise development and noise capture in order to determine the insulation fault location, in full awareness of the sensor locations and taking into account the speed of sonic propagation.

In an embodiment of the method, the measuring-signal impulse sequences are evaluated also analogously to the first method by calculating a correlation of the applied voltage impulse sequence with the measured measuring-signal impulse sequences.

For a subsea supply line, which comprises an outer casing having through bores, the object is attained by a third method, comprising the following method steps: applying electric voltage to ground at the electric conductor, an electrochemical reaction taking place at the insulation fault location between a metallic conductor material of the electric conductor and the seawater, said electrochemical reaction forming gas, and said electric voltage being formed by a modulated voltage impulse sequence; capturing gas bubbles exiting from the through bores of the outer casing by optically sampling immediate surroundings along the subsea supply line using an image capturing system; and evaluating image patterns for identifying a gas-bubble image pattern and for determining the insulation fault location.

In this third embodiment, the notion of the invention is also based on the electrochemical reaction, which is caused by a modulated electric voltage, between the metallic conductor material and the saltine seawater as well as the gas bubble formation resulting therefrom.

In this third method, however, it is not the sonic capture that provides a conclusion to a possible insulation fault location but rather the optical capture of the gas bubbles exiting from the through bores of the outer casing.

For this purpose, the immediate surroundings along the subsea supply line are sampled using a movable image capturing system. The captured image patterns are evaluated with respect to a congruence with typical gas-bubble image patterns impressed by the modulated voltage impulse sequence.

In full awareness of the capture location, the insulation fault location can be determined when a congruence has been identified.

Advantageously, the image patterns are evaluated and the gas-bubble image patterns are identified by calculating a correlation of the applied voltage impulse sequence with a captured gas-bubble image pattern.

In consequence of the characteristic gas bubble patterns impressed by the modulated voltage impulse sequence, these gas bubble patterns can be reliably identified among the captured gas bubbles by calculating the correlation.

The object of the invention is further attained by a respective locating system, which corresponds to the claims according to the invention.

A first locating system executes the first method for determining an insulation fault location on an electric conductor of a subsea supply line, which can be filled with seawater, and consists of the following: a voltage generator for generating a modulated voltage impulse sequence, which is grounded to the electric conductor; sonic sensors, which are installed at predetermined locations along the subsea supply line in order to capture sonic waves propagating within the subsea supply line in the seawater filling; and an evaluation device for evaluating measuring-signal impulse sequences provided by the sonic sensors in order to determine the insulation fault location.

A second locating system executes the second method for determining an insulation fault location on an electric conductor of a subsea supply line, which can be filled with seawater, and consists of the following: a voltage generator for generating a modulated voltage impulse sequence, which can be grounded to the electric conductor; sonic sensors, which are installed at predetermined locations in the seawater filling surrounding the subsea supply line in order to capture sonic waves emitted by the subsea supply line outside of the subsea supply line; and an evaluation device for evaluating measuring-signal impulse sequences provided by the sonic sensors in order to determine the insulation fault location.

A third locating system executes the third method for determining an insulation fault location on an electric conductor of a subsea supply line, which comprises an outer casing having through bores, and consists of the following: a voltage generator for generating a modulated voltage impulse sequence, which is grounded to the electric conductor; an image capturing system, which captures gas bubbles being formed at the insulation fault location and exiting from the through bores by optically sampling immediate surroundings of the subsea supply line; and an image evaluation device for evaluating image patterns in order to identify gas-bubble image patterns and determine the insulation fault location.

In another embodiment, the image capturing system and the image evaluation device are realized as integrated and autonomously navigating image processing systems.

Such an image processing system can optically sample (scan) the subsea supply line in an autonomous manner and communicate the position of the insulation fault location in the event of a fault, i.e. when identifying an expected gas bubble pattern.

BRIEF DESCRIPTION OF THE DRAWING FIGURES

Figure 2:
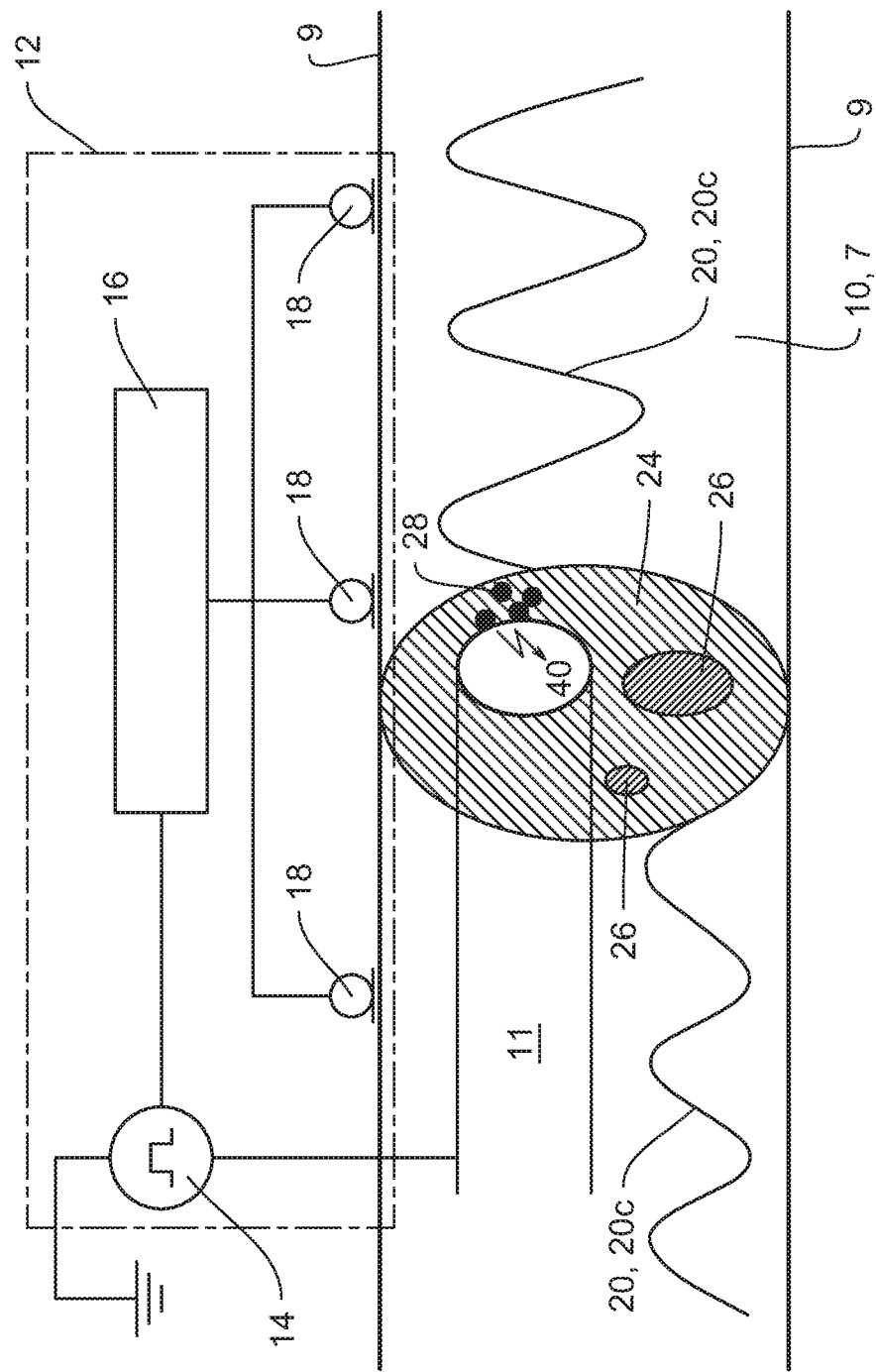
Figure 3:
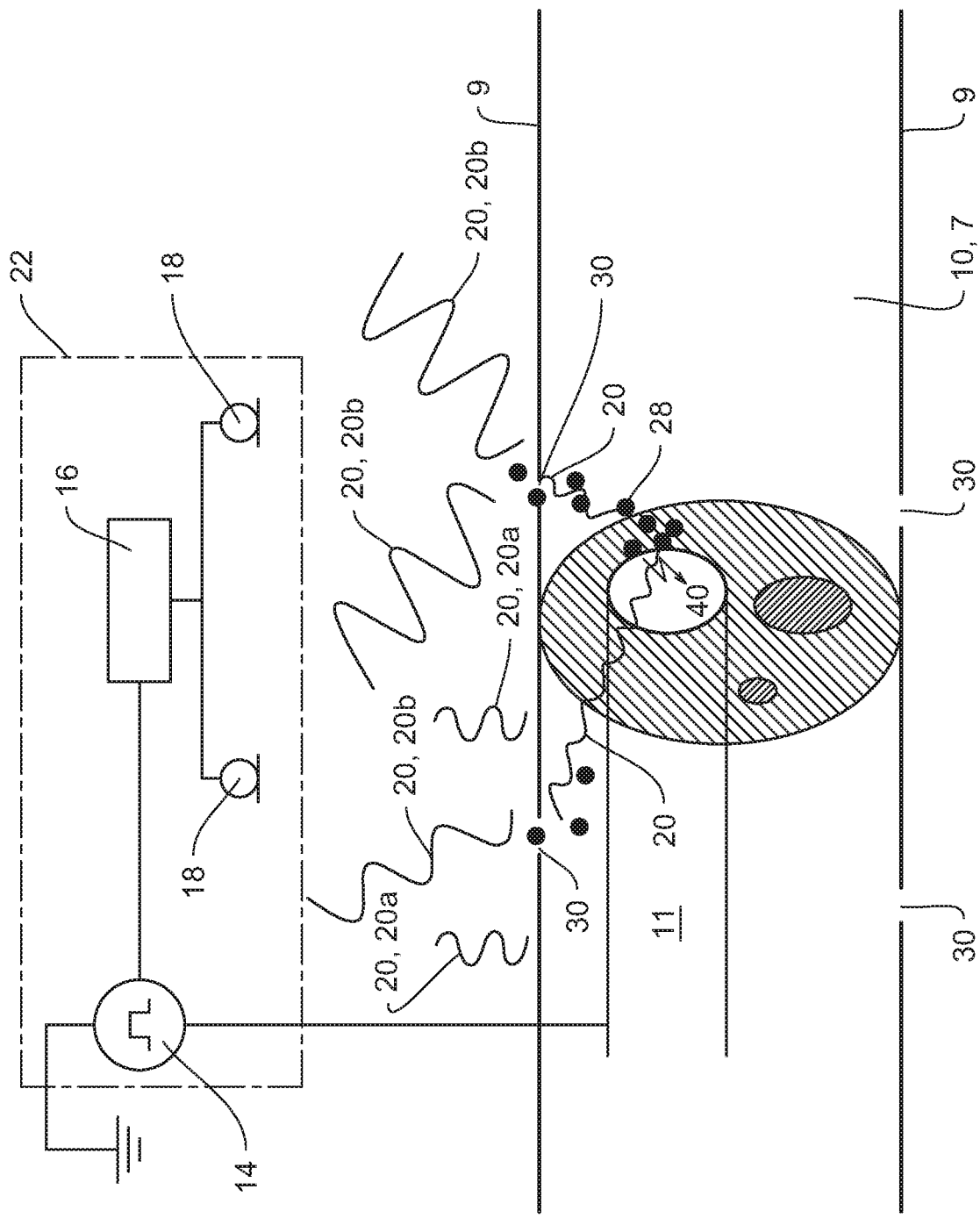
Figure 4:
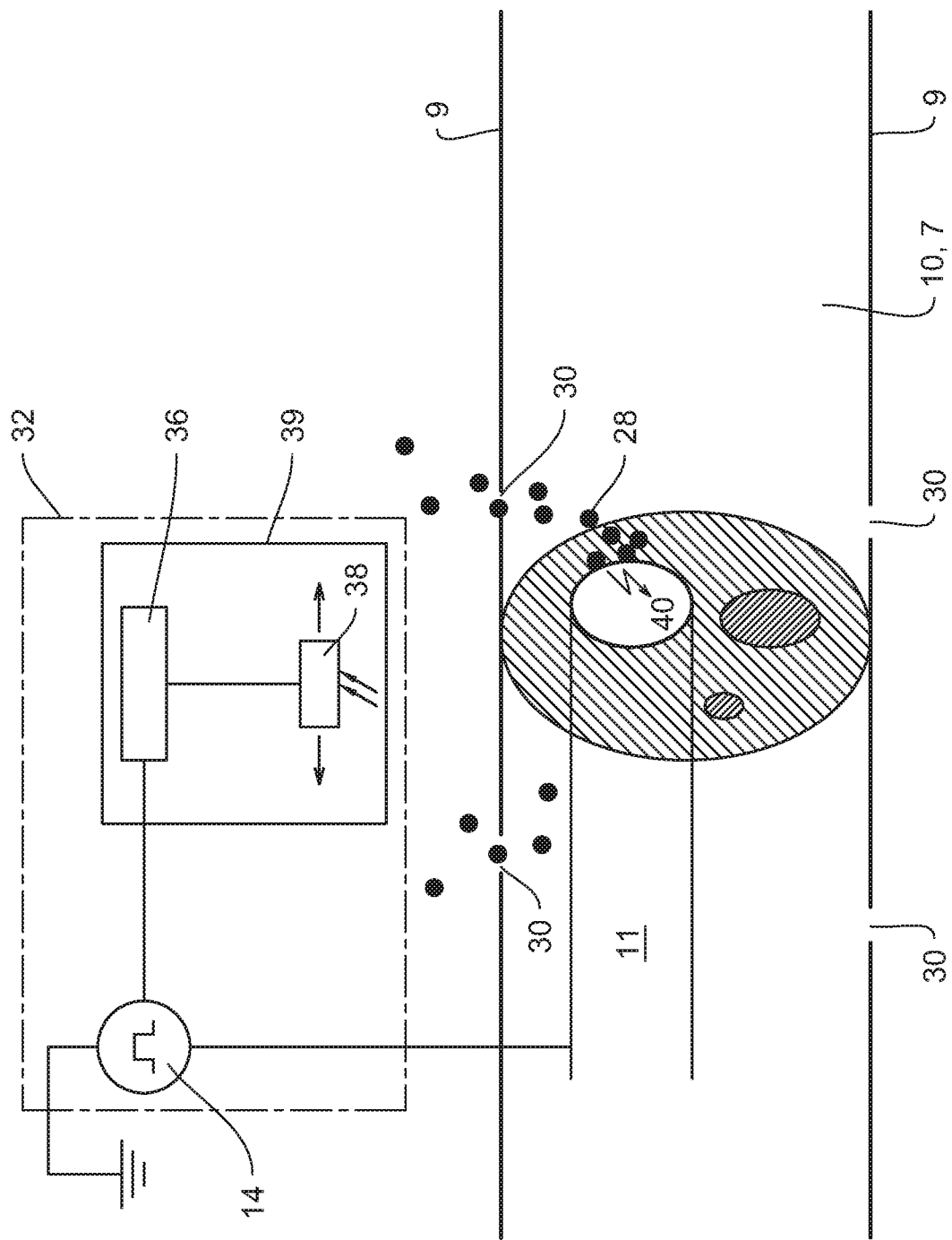

Further advantageous embodiments of the invention can be taken from the following description and the drawings, which explain preferred embodiments of the invention by way of example. In the figures, FIG. 1 shows a schematic overview display regarding the invention's field of application, FIG. 2 shows a schematic display of the first locating system according to the invention, FIG. 3 shows a schematic display of the second locating system according to the invention, and FIG. 4 shows a schematic display of the third locating system according to the invention.

DETAILED DESCRIPTION

FIG. 1 shows the invention's field of application in a schematic overview display. A unit 2 of an oil or gas field on the bottom 4 of the sea is supplied with electric energy, pressure pipelines and command information via subsea supply lines 10 originating from a central production platform 8 placed at the sea surface 6. The subsea supply line 10 comprises an electric conductor 11 for supplying current.

In the overview according to FIG. 1, an exemplary first locating system 12 resting upon the first method is shown, said locating system 12 originating from a subsea supply line 10 flooded with a seawater filling 7 and surrounded by seawater 5.

A voltage generator 14 and an evaluation device 16 of the first locating system 12 are arranged on the production platform 8. Sonic sensors 18 are connected to the evaluation device 16, said sonic sensors 18 being installed at predetermined locations along the subsea supply line 10.

These sonic sensors 18 capture sonic waves 20, which propagate directed within the subsea supply line 10 in the seawater filling 7 originating from an insulation fault location 40 on the electric conductor 11 in this display (first method and first locating system 12, respectively).

FIG. 2 is a schematic display of the first locating system 12 according to the invention.

The locating system 12 comprises the voltage generator 14 for generating electric voltage to ground, which is applied to the electric conductor 11 of the subsea supply line 10, as well as the evaluation device 16 and the sonic sensors 18 arranged outside of the production platform 8.

The subsea supply line 10 flooded with a seawater filling 7 is shown in cross section 24, the electric conductor 11 being shown in the subsea supply line 10 (along with two other conductors 26), an insulation fault 40 having occurred on the electric conductor 11.

Sonic waves 20, 20c propagate directed from the insulation fault location 40 due to gas bubbles 28 forming in the seawater filling 7 of the subsea supply line 10. These sonic waves 20, 20c are captured by sonic sensors 18, which are installed directly on an outer casing 9 of the subsea supply line 10 along the subsea supply line 10. Measuring-signal impulse sequences provided by the sonic sensors 18 are forwarded to the evaluation device 16 in order to determine the insulation fault location 40.

FIG. 3 shows a schematic view of the second locating system 22 according to the invention.

Like the first locating system 12 (FIG. 2), the second locating system 22 comprises the voltage generator 14 for generating electric voltage to ground, which is applied to the electric conductor 11 of the subsea supply line 10, as well as the evaluation device 16 and the sonic sensors 18 arranged outside of the production platform 8.

In this case, the sonic waves 20 generated in consequence of gas bubbles 28 forming in the seawater filling 7 at the insulation fault location 40 on the electric conductor 11 and propagating outside of the subsea supply line 10 are captured using sonic sensors 18. The sonic sensors 18 are thus not directly arranged on the outer casing 9 of the subsea supply line 10 but can rather be installed at some distance to the subsea supply line 10 at suitable locations. Preferred sonic sensors 18, for example, could be highly sensitive microbarometers.

Should the outer casing 9 of the subsea supply line 10 be interspersed with through bores 30 (in order to reduce buoyancy and to simplify installation), then not only would the sonic waves 20a transmitted indirectly via oscillations of the outer casing 9 be directly captured but also the sonic waves 20b emitted by the through bores 30 would be directly captured as well.

FIG. 4 shows a schematic view of the third locating system 32 according to the invention.

The third locating system 32 comprises the voltage generator 14 for generating an electric voltage to ground, which is applied to the electric conductor 11 of the subsea supply line 10, as well as an image evaluation device 36 and an image capturing system 38 arranged outside of the production platform 8.

When using this third locating system 32, a subsea supply line 10 is presumed, whose outer casing 9 comprises through bores 30 and is thus flooded with seawater 5.

In order to capture the gas bubbles 28 exiting from the through bores 30, the immediate surroundings along the subsea supply line 10 are optically sampled (scanned) using a movable image capturing system 38. The captured image patterns are evaluated in the image evaluation device 36 in regard of a congruence with typical gas-bubble image patterns impressed by the modulated voltage impulse sequence.

The image capturing system 38 and the image evaluation device 36 can be realized as an integrated and autonomously navigating image processing system 39, which samples the subsea supply line 10 and tests whether expected gas-bubble image patterns occur.

When gas-bubble image patterns have been identified, the capture location belonging to the gas-bubble image pattern can be communicated as the insulation fault location.

The invention claimed is:

1. A method for determining an insulation fault location (40) on an electric conductor (11) of a subsea supply line (10), which is submerged in seawater (5), comprising the method steps:

applying electric voltage to ground at the electric conductor (11), an electrochemical reaction taking place at the insulation fault location between a metallic conductor material of the electric conductor (11) and the seawater (5), said electrochemical reaction forming gas, and said electric voltage being formed by a modulated voltage impulse sequence, capturing sonic waves (20, 20c) of a noise made by formed gas bubbles (28), sonic waves (20, 20c) of the noise propagating within the subsea supply line (10) in the seawater filling (7) being captured using sonic sensors (18), which are installed at predetermined locations along the subsea supply line (10), evaluating measuring-signal impulse sequences supplied by the sonic sensors (18), and using the signal impulse sequences to determine the insulation fault location (40).

2. The method according to claim 1, characterized in that the measuring-signal impulse sequences are evaluated by calculating a correlation of the applied voltage impulse sequence with the measured measuring-signal impulse sequences.

3. A method for determining an insulation fault location (40) on an electric conductor (11) of a subsea supply line (10), which is submerged in seawater (5), comprising the method steps:

applying electric voltage to ground at the electric conductor (11), an electrochemical reaction taking place at the insulation fault location (40) between a metallic conductor material of the electric conductor (11) and the seawater (5), said electrochemical reaction forming gas, and said electric voltage being formed by a modulated voltage impulse sequence, capturing sonic waves (20, 20*a*, 20*b*) of a noise made by formed gas bubbles (28), sonic waves (20, 20*a*, 20*b*) of the noise being captured outside of the subsea supply line (10) using sonic sensors (18), which are installed at predetermined location in the seawater (5), evaluating measuring-signal impulse sequences supplied by the sonic sensors (18), and using the signal impulse sequences to determine the insulation fault location (40).

4. The method according to claim 3, characterized in that the measuring signal impulse sequences are evaluated by calculating a correlation of the applied voltage impulse sequence with the measured measuring-signal impulse sequences.

5. A method for determining an insulation fault location (40) on an electric conductor (11) of a subsea supply line (10), which comprises an outer casing (9) having through bores (30), comprising the method steps:

applying electric voltage to ground at the electric conductor (11), an electrochemical reaction taking place at the insulation fault location (40) between a metallic conductor material of the electric conductor (11) and the seawater (5), said electrochemical reaction forming gas, said electric voltage being formed by a modulated voltage impulse sequence, capturing gas bubbles (28) exiting from the through bores (30) of the outer casing (9) by optically sampling immediate surroundings along the subsea supply line (10) using an image capturing system (38), evaluating image patterns for identifying a gas-bubble image pattern, and using the gas-bubble image pattern to determine the insulation fault location (40).

6. The method according to claim 5, characterized in that the image patterns are evaluated and the gas-bubble image patterns are identified by calculating a correlation of the applied voltage impulse sequence with a captured gas-bubble image pattern.

7. A locating system for determining an insulation fault location (40) on an electric conductor (11) of a subsea supply line (10), which is submerged in seawater (5), comprising a voltage generator (14) for generating a modulated voltage impulse sequence, which is grounded to the electric conductor (11); comprising sonic sensors (18), which are installed at predetermined locations along the subsea supply line (10) in order to capture sonic waves (20, 20*c*) propagating within the subsea supply line (10) in the seawater filling (7); and comprising an evaluation device (16) for evaluating signal impulse sequences supplied by the sonic sensors (18), and using the signal impulse sequences for determining the insulation fault location (40).

8. A locating system for determining an insulation fault location (40) on an electric conductor (11) of a subsea supply line (10), which is submerged in seawater (5), comprising a voltage generator (14) for generating a modulated voltage impulse sequence, which is grounded to the electric conductor (11); comprising sonic sensors (18), which are installed at predetermined locations in the seawater (5) surrounding the subsea supply line (10) in order to capture sonic waves (20, 20*a*, 20*b*) emitted from the subsea supply line (10) outside of the subsea supply line (10); and comprising an evaluation device (16) for evaluating signal impulse sequences supplied by the sonic sensors (18) and using the signal impulse sequences for determining the insulation fault location (40).

9. A tracking device for determining an insulation fault location (40) on an electric conductor (11) of a subsea supply line (10), which comprises an outer casing (9) having through bores (30), comprising a voltage generator (14) for generating a modulated voltage impulse sequence, which is grounded to the electric conductor (11); comprising an image capturing system (38), which captures gas bubbles (28) being formed at the insulation fault location (40) and exiting from the through bores (30) by optically sampling immediate surroundings of the subsea supply line (10); and comprising an image evaluation device (36) for evaluating image patterns in order to identify gas-bubble image patterns; and using the gas-bubble image patterns to determine the insulation fault location (40).

10. The tracking device according to claim 9, characterized in that the image capturing system (38) and the image evaluation device (36) are configured as an integrated, autonomously navigating imaging system (39).

* * * * *